United States Patent [19]

Bellina

[11] 4,151,296

[45] Apr. 24, 1979

[54] BUTYRAMIDES AND BUTYRATES

[75] Inventor: Russell F. Bellina, Wilmington, Del.

[73] Assignee: E. I. Du Pont de Nemours and Company, Wilmington, Del.

[21] Appl. No.: 845,052

[22] Filed: Oct. 25, 1977

Related U.S. Application Data

[60] Division of Ser. No. 463,987, Apr. 25, 1974, Pat. No. 4,059,623, which is a continuation-in-part of Ser. No. 369,606, Jun. 13, 1973, abandoned.

[51] Int. Cl.$^2$ .................... A01N 9/00; A01N 9/20; A01N 9/22
[52] U.S. Cl. ................... 424/298; 424/244; 424/248.54; 424/248.56; 424/250; 424/267; 424/274; 424/300; 424/320
[58] Field of Search ............... 424/298, 327, 300, 320, 424/244, 248.54, 248.56, 250, 267, 274

[56] References Cited

U.S. PATENT DOCUMENTS

| | | | |
|---|---|---|---|
| 2,542,812 | 2/1951 | Hartung | 260/561 A |
| 3,849,481 | 11/1974 | Fuhrmann et al. | 260/561 A |

Primary Examiner—Allen J. Robinson

[57]  ABSTRACT

Substituted 2-(carbamoyl)oxyimino-3-iminobutyramides and 2-(carbamoyl)oxyimino-3-iminobutyrates of the formula

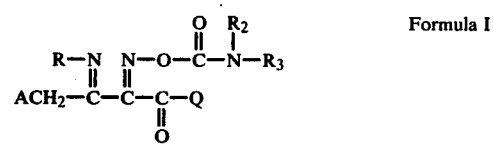

Formula I where Q is —OR$_4$ or —NR$_5$R$_6$, and A, R, R$_2$, R$_3$, R$_4$, R$_5$, and R$_6$ are as hereinafter defined are useful as aphicides. The compounds are made by reacting an amine with a substituted 2-hydroxyiminoacetoacetamide (or 2-hydroxyiminopropionylacetamide) or an alkyl 2-hydroxyiminoacetoacetate (or 2-hydroxyiminopropionylacetate), then carbamylating the resulting substituted 2-hydroxyimino-3-iminobutyramide (or 2-hydroxyimino-3-iminovaleramide) or 2-hydroxyimino-3-iminobutyrate (or 2-hydroxyimino-3-iminovalerate).

14 Claims, No Drawings

BUTYRAMIDES AND BUTYRATES

CROSS REFERENCE TO RELATED APPLICATIONS

This application is a division of application Ser. No. 463,987, filed Apr. 25, 1974, now U.S. Pat. No. 4,059,623, which in turn is a continuation-in-part of application Ser. No. 369,606, filed June 13, 1973, now abandoned.

BACKGROUND OF THE INVENTION

Buchanan, U.S. Pat. No. 3,530,220, issued Sept. 22, 1970, discloses a class of alkyl 1-carbamoyl-N-(substituted carbamoyloxy)thioformimidates such as methyl 1-(dimethylcarbamoyl)-N-(methylcarbamoyloxy)thioformimidate (oxamyl) which can be represented by the formula $$\begin{array}{c} CH_3 \\ \phantom{CH_3}\diagdown \\ \phantom{CH_3}N-\overset{O}{\overset{\|}{C}}-C=N-O-\overset{O}{\overset{\|}{C}}-N\diagup^{H} \\ CH_3 \diagup \phantom{N-C} \underset{SCH_3}{|} \phantom{-O-C-N} \diagdown CH_3 \end{array}$$

The compounds are useful as nematocides, acaricides and insecticides.

Fuchs and Loux, U.S. Pat. No. 3,694,431, issued Sept. 26, 1972, discloses a method of making the compounds of U.S. Pat. No. 3,530,220 which involves nitrosating an acetoacetamide to produce a 2-hydroxyiminoacetoacetamide, e.g.

$$CH_3-\overset{O}{\overset{\|}{C}}-CH_2-\overset{O}{\overset{\|}{C}}-N\diagup^{CH_3}_{\diagdown CH_3} + HONO \longrightarrow$$

$$CH_3-\overset{O}{\overset{\|}{C}}-\underset{\underset{NOH}{\|}}{C}-\overset{O}{\overset{\|}{C}}-N\diagup^{CH_3}_{\diagdown CH_3}$$

then chlorinating, reacting with a mercaptan, and carbamylating. The 2-hydroxyiminoacetoacetamides are also starting materials for making the substituted 2-hydroxyimino-3-iminobutyramides of the present invention.

Buchanan U.S. Pat. No. 3,557,190, issued Jan. 19, 1971, discloses a method of making the compounds of U.S. Pat. No. 3,530,220 which involves reacting a 2-hydroxyimino ester with two moles of an amine in the presence of water or an alcohol to give the corresponding amide. The amide is then reacted further to give the desired compounds, e.g., $$CH_3S\overset{NOH}{\overset{\|}{-C}}-\underset{\underset{O}{\|}}{C}OC_2H_5 + HN(CH_3)_2 \longrightarrow$$

$$CH_3S-\overset{NOH}{\overset{\|}{C}}-\underset{\underset{O}{\|}}{C}N(CH_3)_2$$

This amination procedure also is useful for the conversion of the 3-imino-2-hydroxyiminoacetoacetates and propionylacetates of this invention to the corresponding 2-hydroxyimino-3-iminobutyramides and 2-hydroxyimino-3-iminovaleramides.

Beilstein, Organische Chemie, Vol. III, Fourth Edition, page 745, discloses α,β-dioximino-butyric acid ethyl ester (A), α,β-dioximino-butyric acid amide (B), ethyl α-oximino-acetoacetate phenylhydrazone (C), ethyl α-acetoximino-acetoacetate (D), and ethyl α-acetoximino-acetoacetate phenylhydrazone (E), compounds which can be represented by the formulae:

$$\begin{array}{c} HO-N \phantom{XX} N-OH \\ \overset{\|}{\phantom{X}} \phantom{XX} \overset{\|}{\phantom{X}} \\ CH_3-C-C-\underset{\underset{O}{\|}}{C}-OC_2H_5 \end{array} \quad (A)$$

$$\begin{array}{c} HO-N \phantom{XX} N-OH \\ \overset{\|}{\phantom{X}} \phantom{XX} \overset{\|}{\phantom{X}} \\ CH_3-C-C-\underset{\underset{O}{\|}}{C}-NH_2 \end{array} \quad (B)$$

$$\begin{array}{c} C_6H_5HN-N \phantom{XX} N-OH \\ \overset{\|}{\phantom{X}} \phantom{XX} \overset{\|}{\phantom{X}} \\ CH_3-C-C-\underset{\underset{O}{\|}}{C}-OC_2H_5 \end{array} \quad (C)$$

$$\begin{array}{c} \phantom{XXXXX} O \\ \phantom{XXXXX} \| \\ \phantom{XX} O \phantom{X} N-O-CCH_3 \\ \phantom{XX} \| \phantom{XX} \| \\ CH_3-C-C-\underset{\underset{O}{\|}}{C}-OC_2H_5 \end{array} \quad (D)$$

$$\begin{array}{c} \phantom{XXXXX} O \\ \phantom{XXXXX} \| \\ C_6H_5NH-N \phantom{X} N-O-CCH_3 \\ \phantom{XXX} \| \phantom{XXX} \| \\ CH_3-C-C-\underset{\underset{O}{\|}}{C}-OC_2H_5 \end{array} \quad (E)$$

No utility is disclosed for compounds (A)–(E) in the Beilstein reference.

SUMMARY OF THE INVENTION

This invention is a class of novel aphicidal substituted 2-(carbamoyl)oxyimino-3-iminobutyramides and alkyl 2-(carbamoyl)oxyimino-3-iminobutyrates of the formula:

$$\begin{array}{c} \phantom{XXX} O \phantom{X} R_2 \phantom{XXXXXX} \text{Formula I} \\ \phantom{XXX} \| \phantom{X} | \\ R-N \phantom{X} N-O-C-N-R_3 \\ \overset{\|}{\phantom{X}} \phantom{XX} \overset{\|}{\phantom{X}} \\ ACH_2-C-C-\underset{\underset{O}{\|}}{C}-Q \end{array}$$

wherein:

A is hydrogen or methyl;

R is $C_1$–$C_{18}$ alkyl; $C_3$–$C_4$ alkenyl; $C_5$–$C_7$ cycloalkyl optionally substituted with methoxy or with 1 or 2 methyl groups; $C_6$–$C_8$ cycloalkylalkyl; $C_1$–$C_3$ alkoxy; alkoxyalkyl with a total of 3–6 carbon atoms; benzyl; phenethyl; $(CH_3)_2N-$; $(CH_3)C_2H_5N-$; $(C_2H_5)_2N-$; 1-(4-methylpiperazinyl); N-morpholino;

$$CH_3NH\overset{O}{\overset{\|}{C}}-O-; (CH_3)_2N\overset{O}{\overset{\|}{C}}-O-; \text{ or}$$

-continued

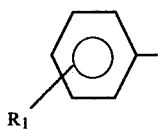

wherein: $R_1$ is hydrogen, methyl, methoxy, $(CH_3)_2N—$, $CH_3S—$, or fluorine;
  $R_2$ is hydrogen, methyl, or ethyl;
  $R_3$ is methyl, ethyl, or allyl;
  Q is $—OR_4$ or $—NR_5R_6$ wherein:
  $R_4$ is $C_1-C_2$ alkyl;
  $R_5$ is methoxy, $C_1-C_4$ alkyl or allyl;
  $R_6$ is hydrogen, methyl, or ethyl; and
  $R_5$ and $R_6$ can be taken together to form a ring and are

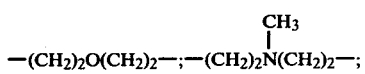

or $—(CH_2)_n—$ where n is 4–6, with the provisos that
  (i) the total carbon content of Q, $R_2$, and $R_3$ is not greater than 8C;
  (ii) when R is

$R_2$ is hydrogen and $R_3$ is $CH_3$; and
  (iii) when R is

$R_2$ and $R_3$ are both methyl.

This invention includes a method of protecting plants from aphids by application of a compound of Formula I and formulations for agricultural use consisting essentially of an inert diluent and/or a surfactant and means for controlling aphids selected from compounds of Formula I.

The invention also includes a novel process, described hereinbelow, for producing the compounds of Formula I.

For each of the compounds of Formula I, there are theoretically four geometric isomers.

DESCRIPTION OF THE INVENTION

Preferred for economic reasons are those compounds of Formula I wherein:
A is hydrogen;
R is $C_5-C_7$ cycloalkyl, methylcyclohexyl, allyl, methoxy, $(CH_3)_2N—$, N-morpholino,

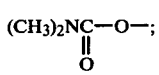

$R_2$ is hydrogen, methyl, or ethyl;
$R_3$ is methyl; and
Q is $—NR_5R_6$ where $R_5$ is methyl or ethyl and
$R_6$ is hydrogen, methyl, or ethyl.

More preferred because of higher aphicidal activity are those compounds of Formula I wherein
A is hydrogen;
R is methoxy or $(CH_3)_2N—$;
$R_2$ is hydrogen, methyl, or ethyl;
$R_3$ is methyl; and
Q is $—NR_5R_6$ wherein
$R_5$ is methyl or ethyl and
$R_6$ is hydrogen, methyl, or ethyl.

Most preferred for highest aphicidal activity are the following compounds of Formula I:
  N,N-dimethyl-2,3-bis[(dimethylcarbamyl)oxyimino]butyramide
  N,N-dimethyl-2-[(methylcarbamyl)oxyimino]-3-(2-methylcyclohexylimino)butyramide
  N,N-dimethyl-2-[(dimethylcarbamyl)oxyimino]-3-dimethylhydrazonobutyramide
  N,N-dimethyl-2-[(methylcarbamyl)oxyimino]-3-(N-morpholine)iminobutyramide
  N,N-dimethyl-2-[(dimethylcarbamyl)oxyimino]-3-(N-morpholine)iminobutyramide
  N,N-dimethyl-3-methoxyimino-2-[(methylcarbamyl)oxyimino]butyramide
  N,N-dimethyl-2-](dimethylcarbamoyl)oxyimino]-3-methoxyiminobutyramide

Compound Synthesis

The compounds of Formula I can be prepared by the following steps:

[$R_7$ is —OH, $C_1-C_{18}$ alkyl, $C_3-C_4$ alkenyl, $C_5-C_7$ cycloalkyl optionally substituted with methoxy or with 1 or 2 methyl groups; $C_6-C_8$ cycloalkylalkyl; $C_1-C_3$ alkoxy; alkoxyalkyl with a total of 3-6 carbon atoms; benzyl; phenethyl; $(CH_3)_2N—$; $(CH_3)C_2H_5N—$; $(C_2H_5)_2N—$; 1-(4-methylpiperazinyl); N-morpholino; or

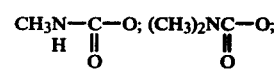

or

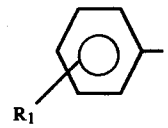

wherein $R_1$ is hydrogen, methyl, methoxy, $(CH_3)_2N—$, $CH_3S—$, or fluorine]

1.a. Reacting an amine of the formula $R_7NH_2$ with a 2-hydroxyiminoacetoacetamide or 2-hydroxyiminoacetoacetate of the formula:

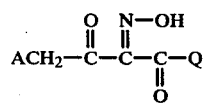
  Formula III wherein A and Q are as defined for Formula I with the added proviso
  (i) if Q is $—NR_5R_6$, A is hydrogen to produce a substituted 2-hydroxyimino-3-iminobutyramide or 2-hydroxyimino-3-iminobutyrate of the formula:

$$R_7-N \quad N-OH$$
$$\| \quad \|$$
$$ACH_2-C-C-C-Q$$
$$\| $$
$$O$$

Formula II 1.b. An alternative route for the synthesis of 2-hydroxyimino-3-iminobutyramides of Formula II (where A is hydrogen and Q is $-NR_5R_6$) and a preferred route for the synthesis of 2-hydroxyimino-3-iminovaleramides of Formula II (where A is methyl and Q is $-NR_5R_6$) is carried out by aminating the esters obtained in Step 1.a., following the Buchanan amination procedure, U.S. Pat. No. 3,557,190, referred to previously.

2. Carbamylating the compound of Formula II by reacting it with one mole of a carbamylating agent selected from a. an isocyanate of the formula $R_3NCO$ and b. a base and a dialkylcarbamoyl chloride of the formula $$\underset{\|}{O}$$
$$ClCNR_2R_3$$

wherein $R_2$ in $$\underset{\|}{O}$$
$$ClCNR_2R_3$$

is methyl or ethyl, provided that when $R_7$ is $-OH$, $R_3$ in $R_3NCO$ is methyl, $R_2$ and $R_3$ in $$\underset{\|}{O}$$
$$ClCNR_2R_3$$

are both methyl, and two moles of the carbamylating agent are reacted.

The processes can be represented schematically as follows:

1.a.
$$ACH_2-C-C-C-Q + R_7NH_2 \longrightarrow$$

$$ACH_2-C-C-C-Q + H_2O$$

1.b.
$$ACH_2-C-C-COR_4 + HNR_5R_6 \longrightarrow$$

$$ACH_2C-C-C-NR_5R_6 + R_4OH$$

2. (when $R_7$ is not $-OH$)

a.
$$ACH_2-C-C-C-Q + R_3NCO \longrightarrow$$

$$R_7-N \quad N-O-C-NHR_3$$
$$ACH_2-C-C-C-Q$$

b.
$$ACH_2-C-C-C-Q + \begin{array}{l} 1)\ base \\ 2)\ R_2R_3NCCl \end{array} \longrightarrow$$

$$R_7-N \quad N-O-C-N(R_2)(R_3)$$
$$ACH_2-C-C-C-Q$$

2. (when $R_7$ is $-OH$)

a.
$$HO-N \quad N-OH$$
$$ACH_2-C-C-Q + 2CH_3NCO \longrightarrow$$

$$CH_3N-C-O-N \quad N-O-C-NHCH_3$$
$$ACH_2-C-C-C-Q$$

b.
$$HO-N \quad N-OH$$
$$ACH_2-C-C-C-Q + 2 \begin{array}{l} 1)\ base \\ 2)\ (CH_3)_2NC-Cl \end{array} \longrightarrow$$

$$(CH_3)_2N-C-O-N \quad N-O-C-N(CH_3)_2$$
$$ACH_2-C-C-C-Q$$

The starting 2-hydroxyiminoacetoacetamides of Formula III (A=hydrogen and Q=$-NR_5R_6$) can be prepared by the process described in Fuchs and Loux, U.S. Pat. No. 3,694,431, issued Sept. 26, 1972. The process involves reacting diketene with an amine ($NHR_5R_6$) to produce a substituted acetoacetamide, then nitrosating the acetoacetamide by reaction with a source of nitrous acid, e.g., sodium nitrite and HCl.

The starting alkyl 2-hydroxyiminoacetoacetates or alkyl 2-hydroxyiminopropionylacetates of Formula III (Q=$-OR_4$) can be made as described by Rodinov et al. [*J. Gen. Chem.*, USSR 18, 917 (1948)]. An aqueous solution of sodium nitrite is slowly added to an acetic acid solution of the acetoacetate or propionylacetate at low temperature. Modifications of this synthesis are described in German Patent No. 1,137,434 and Belgian Patent No. 610,194.

In Step 1.a., the amine can be used directly as a free base or it may be used as a salt in which the free base is released for reaction by using an alkali metal carbonate or a tertiary amine such as pyridine for this purpose. Typical amines used for this step are methylamine, ethylamine, sec-butylamine, octylamine, methoxyamine hydrochloride, ethoxyamine hydrochloride, hydroxylamine hydrochloride (a special case where the product, a 2,3-dioxime derivative is used to make products where R is

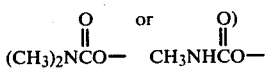

p-anisidine, aniline, N-aminomorpholine, and 1,1-dimethylhydrazine. When the amine is an aniline or a high-boiling amine, provision is often made for removal of by-product water. Details of these variations will be shown with specific examples which follow. The Step 1 reaction can be carried out under the following general conditions: time, 1 to 72 hours, preferably 2 to 18 hours; temperature, 5° to 140° C., preferably 20° to 85° C.; pressure, ½ to 10 atmospheres, preferably 1 atmosphere; medium, inert organic solvent such as ethanol, methanol, benzene, toluene, or water, in some cases, where the intermediate is water soluble.

For Step 1.b., both the starting 2-hydroxyiminoacetamides and 2-hydroxyiminopropionylvaleramides of Formula II (A=hydrogen and methyl, respectively, and Q=—$NR_5R_6$) can be made by aminating the corresponding acetoacetates and propionylacetates obtained in Step 1. of Formula III (Q=—$OR_4$) essentially as described in Buchanan U.S. Pat. No. 3,557,190, issued Jan. 19, 1971. The process involves reacting a substituted 2-hydroxyiminoacetate ester with an amine in the presence of water and/or lower alcohol ($C_1$-$C_3$). Two moles of a primary or secondary amine are necessary because one mole forms a salt with the hydroxyimino function while another mole participates directly in the reaction. A tertiary amine such as triethylamine can be substituted for these amines with about the same results. In a few instances, no solvent other than excess amine is used. A catalytic amount of sodium methylate can be used to accelerate this reaction.

The products can be isolated in a conventional manner by filtration or evaporation of the solvent. It is desirable to isolate these products or at least to remove any excess amine prior to performing the carbamylation step (Step 2).

In Step 2.a., the reaction is often catalyzed with a tertiary amine such as triethylamine, pyridine, or triethylenediamine and/or a tin catalyst such as dibutyl-tin dilaurate. The ratio of reactants is generally stoichiometric, although a slight excess of the isocyanate is sometimes desirable. The following general conditions can be used: time, one-half to 72 hours, preferably 1 to 4 hours; temperature, 5° to 140° C., preferably 20° to 110° C.; pressure, one-half to 10 atmospheres, preferably 1 atmosphere; reaction medium, inert organic solvent such as acetone, acetonitrile, methyl ethyl ketone, dimethylformamide, or methylene chloride. After the reaction, removal of the solvent gives a residual product which often is of satisfactory quality for its application. If the product is a solid, it can be purified by recrystallization from a suitable solvent. Several of the residues are oils which are very slow to crystallize, particularly in the ester series, so that other conventional purification procedures must be used.

In the Step 2.b. and 3.b. reactions, a sodium salt is first formed by portionwise addition of sodium methoxide or of a mineral oil dispersion of sodium hydride to a solution of the intermediate in an inert organic solvent such as tetrahydrofuran, dioxane, benzene, or toluene. The temperature is maintained in the range of about 5° to 60° C., preferably 15° to 35° C., until, in the case of the hydride, evolution of hydrogen ceases. Other salts, such as the trimethylamine and triethylamine salts, also work satisfactorily. Reaction of the carbamoyl chloride with the salt can be carried out under the following general conditions: time, one-half to 72 hrs., preferably 1-4 hrs., temperature, 5°-140° C., preferably 20°-65° C.; pressure, ½-10 atmospheres, preferably 1 atmosphere. After separation from the reaction medium, the product is obtained usually in sufficiently pure condition to be used as an aphicide; however, the usual purification procedures can be used if desired.

The procedures for synthesis of the compounds of this invention are further illustrated in the following examples wherein parts and percentages are by weight unless otherwise noted.

EXAMPLE 1

To a stirred mixture of 336 parts of N,N-dimethyl-2-hydroxyiminoacetoacetamide (a compound of Formula III), 1500 parts ethanol and 203 parts of methoxyamine hydrochloride were added dropwise 210 parts of pyridine over one-half hour while maintaining the reaction mixture at 10° C. by external cooling. The mixture was allowed to warm slowly to 25° C. and maintained at this temperature for 18 hours. Finally, it was stirred and refluxed for one-half hour. The solvent was removed under reduced pressure (15 mm.) at 40° C. bath temperature. Approximately 2000 parts of ice water were added, which caused the residue to solidify. The solid was filtered, washed twice with ice water, filtered, and dried. There was obtained 340 parts of N,N-dimethyl-2-hydroxyimino-3-methoxyiminobutyramide (a compound of Formula II), m.p. 144–147, which is of satisfactory quality for use as an intermediate. The product was, however, recrystallized from ethyl acetate, whereupon it melted at 146°–148°.

This procedure can be repeated by substituting comparable molar amounts of the indicated compound of Formula III in Table I below and the amine (either used as free amine or released through use of pyridine or sodium carbonate) to produce the indicated compound of Formula II. A slight-to-moderate excess of amine is desirable for best yields (one to two moles amine per mole of compound of Formula III). External heating is not always required, especially when the reaction is exothermic.

TABLE I

| Compound of Formula III | | | Compound of Formula II | | Compound of Formula I | | | Melting Point |
|---|---|---|---|---|---|---|---|---|
| $$ACH_2C \overset{O}{\underset{\|}{-}} C \overset{NOH}{\underset{\|}{-}} Q$$ with C=O | | | $$ACH_2C \overset{R_7-N}{\underset{\|}{-}} C \overset{NOH}{\underset{\|}{-}} Q$$ with C=O | | $$ACH_2 \overset{R-N}{\underset{\|}{-}} C \overset{O}{\underset{\|}{-}} NOC \overset{R_2}{\underset{\|}{-}} N-R_3 \,\, -Q$$ with C=O | | | |
| A | Q | Amine | $R_7$, R of Form. I | Isocyanate | $R_2$ | $R_3$ | | (° C.) |
| H | —$N(CH_3)_2$ | $CH_3ONH_2$—HCl | $CH_3O$ | $C_2H_5NCO$ | H | $C_2H_5$— | | 87–89 |
| H | —$N(CH_3)_2$ | $CH_3ONH_2$—HCl | $CH_3O$ | $CH_2=CHCH_2NCO$ | H | $CH_2=CHCH_2$— | | 66–68 |
| $CH_3$ | —$N(CH_3)_2$ | $CH_3ONH_2$—HCl | $CH_3O$ | $CH_3NCO$ | H | $CH_3$— | | |

TABLE I-continued

| Compound of Formula III | | Amine | Compound of Formula II | Isocyanate | Compound of Formula I | | Melting Point (°C.) |
|---|---|---|---|---|---|---|---|
| A | Q | | $R_7$, R of Form. I | | $R_2$ | $R_3$ | |
| H | $-N(CH_3)_2$ | $C_2H_5ONH_2-HCl$ | $C_2H_5O-$ | $CH_3NCO$ | H | $CH_3-$ | 139.5–140.5 |
| H | $-N(CH_3)_2$ | $C_2H_5ONH_2-HCl$ | $C_2H_5O-$ | $C_2H_5NCO$ | H | $C_2H_5-$ | |
| H | $-N(CH_3)_2$ | $C_2H_5ONH_2-HCl$ | $C_3H_7O-$ | $CH_3NCO$ | H | $CH_3-$ | |
| $CH_3$ | $-NHCH_3$ | $CH_3ONH_2-HCl$ | $CH_3O-$ | $CH_3NCO$ | H | $CH_3-$ | 169–173 |
| H | $-NHCH_3$ | $CH_3ONH_2-HCl$ | $CH_3O-$ | $CH_3NCO$ | H | $CH_3-$ | 169–173 |
| H | $-NHCH_3$ | $CH_3ONH_2-HCl$ | $CH_3O-$ | $C_2H_5NCO$ | H | $C_2H_5-$ | |
| H | $-OC_2H_5$ | $CH_3ONH_2-HCl$ | $CH_3O-$ | $CH_3NCO$ | H | $CH_3-$ | |
| H | $-OC_2H_5$ | $C_2H_5ONH_2-HCl$ | $C_2H_5O-$ | $CH_2=CHCH_2NCO$ | H | $CH_2=CHCH_2-$ | |
| H | $-OCH_3$ | $CH_3ONH_2-HCl$ | $CH_3O$ | $C_2H_5NCO$ | H | $C_2H_5-$ | |
| H | $-OCH_3$ | $CH_3ONH_2-HCl$ | $CH_3O$ | $CH_3NCO$ | H | $CH_3-$ | |
| H | $-NHC_2H_5$ | $CH_3ONH_2-HCl$ | $CH_3O-$ | $CH_3NCO$ | H | $CH_3-$ | |
| $CH_3$ | $-NHC_2H_5$ | $CH_3ONH_2-HCl$ | $CH_3O-$ | $C_2H_5NCO$ | H | $C_2H_5-$ | |
| H | $-NHC_3H_7$ | $C_2H_5ONH_2-HCl$ | $C_2H_5O-$ | $CH_3NCO$ | H | $CH_3-$ | |
| H | $-NHC_4H_9$ | $CH_3ONH_2-HCl$ | $CH_3O-$ | $CH_3NCO$ | H | $CH_3-$ | 125–128 |
| H | $-NHC_4H_9$ | $CH_3ONH_2-HCl$ | $CH_3O-$ | $C_2H_5NCO$ | H | $C_2H_5$ | 138–140 |
| H | $-NHCH(CH_3)_2$ | $CH_3ONH_2-HCl$ | $CH_3O$ | $CH_3NCO$ | H | $CH_3-$ | |
| H | $-N(C_2H_5)_2$ | $CH_3ONH_2-HCl$ | $CH_3O$ | $CH_3NCO$ | H | $CH_3-$ | 118–120 |
| H | $-N(C_2H_5)(CH_2CH=CH_2)$ | $CH_3ONH_2-HCl$ | $CH_3O$ | $CH_3NCO$ | H | $CH_3-$ | |
| $CH_3$ | $-OC_2H_5$ | $CH_3NH_2$ | $CH_3-$ | $CH_3NCO$ | H | $CH_3-$ | |
| H | morpholino | $CH_3ONH_2-HCl$ | $CH_3O$ | $CH_3NCO$ | H | $CH_3-$ | 137–140 |
| H | 4-methylpiperazino | $CH_3ONH_2-HCl$ | $CH_3O$ | $CH_3NCO$ | H | $CH_3-$ | |
| H | $-N(CH_3)(OCH_3)$ | $CH_3ONH_2-HCl$ | $CH_3O$ | $CH_3NCO$ | H | $CH_3-$ | 99–103 |
| H | $-N(CH_3)(OCH_3)$ | $CH_3ONH_2-HCl$ | $CH_3O$ | $C_2H_5NCO$ | H | $C_2H_5-$ | 97.5–101 |
| H | pyrrolidino | $CH_3NH_2$ | $CH_3-$ | $CH_3NCO$ | H | $CH_3-$ | |
| H | piperidino | $(CH_3)_2CHONH_3-HCl$ | $(CH_3)_2CHO-$ | $CH_3NCO$ | H | $CH_3-$ | |
| H | piperidino | $C_4H_9NH_2$ | $C_4H_9-$ | $C_2H_5NCO$ | H | $C_2H_5-$ | |
| H | $N(CH_3)_2$ | $(CH_3)_2NNH_2$ | $(CH_3)_2N-$ | $CH_3NCO$ | H | $CH_3-$ | 146–148 |
| H | $N(CH_3)_2$ | morpholino-$NH_2$ | morpholino-$N-$ | $CH_3NCO$ | H | $CH_3-$ | 141–142.5 |
| H | $N(CH_3)_2$ | morpholino-$NH_2$ | morpholino-$N-$ | $C_2H_5NCO$ | H | $C_2H_5-$ | 128–130 |
| $CH_3$ | $N(CH_3)_2$ | $(CH_3)_2NNH_2$ | $(CH_3)_2N-$ | $CH_3NCO$ | H | $CH_3-$ | |
| H | $N(CH_3)_2$ | morpholino-$NH_2$ | morpholino-$N-$ | $CH_3NCO$ | H | $CH_3-$ | 128–129 (dec) |
| H | $N(CH_3)_2$ | $CH_2=CHCH_2NH_2$ | $CH_2=CHCH_2-$ | $CH_3NCO$ | H | $CH_3-$ | |
| H | $N(CH_2)_2$ | cyclopropyl-$NH_2$ | cyclopropyl- | $CH_3NCO$ | H | $CH_3-$ | |
| H | $N(CH_3)_2$ | cyclohexyl-$NH_2$ | cyclohexyl- | $CH_3NCO$ | H | $CH_3-$ | |
| H | $N(CH_3)_2$ | $CH_3N$-piperazino-$NH_2$ | $CH_3N$-piperazino-$N-$ | $CH_3NCO$ | H | $CH_3-$ | |
| H | $N(CH_3)_2$ | $CH_3NH_2$ | $CH_3-$ | $CH_3NCO$ | H | $CH_3-$ | 135–137 |
| H | $N(CH_3)_2$ | $CH_3NH_2$ | $CH_3-$ | $C_2H_5NCO$ | H | $C_2H_5$ | |
| H | $N(CH_3)_2$ | $C_2H_5NH_2$ | $C_2H_5-$ | $CH_3NCO$ | H | $CH_3-$ | 135–138 |
| H | $N(CH_3)_2$ | $C_3H_7NH_2$ | $C_3H_7-$ | $CH_3NCO$ | H | $CH_3-$ | 130–132 |

TABLE I-continued

| Compound of Formula III $$ACH_2\overset{\overset{O}{\|}}{C}-\overset{\overset{NOH}{\|}}{C}-Q$$ | | | Compound of Formula II $$ACH_2\overset{\overset{R_7-N}{\|}}{C}-\overset{\overset{NOH}{\|}}{C}-\overset{\overset{}{\|}}{C}-Q$$ $$\phantom{xxxxxxxx}O$$ | | Compound of Formula I $$ACH_2-\overset{\overset{R-N}{\|}}{C}-\overset{\overset{NOC-N-R_3}{\|}}{C}-\overset{\overset{O\;R_2}{\|}}{C}-Q$$ $$\phantom{xxxxxxxxxxx}O$$ | | Melting Point |
|---|---|---|---|---|---|---|---|
| A | Q | Amine | $R_7$, R of Form. I | Isocyanate | $R_2$ | $R_3$ | (° C.) |
| H | $N(CH_3)_2$ | $(CH_3)_2CHNH_2$ | $(CH_3)_2CH-$ | $CH_3NCO$ | H | $CH_3-$ | 158–159 |
| H | $N(CH_3)_2$ | $C_2H_5\underset{\underset{CH_3}{\|}}{C}HNH_2$ | $C_2H_5\underset{\underset{CH_3}{\|}}{C}H-$ | $CH_3NCO$ | H | $CH_3-$ | 139–141 |
| H | $N(CH_3)_2$ | $C_6H_{13}NH_2$ | $C_6H_{13}-$ | $CH_3NCO$ | H | $CH_3-$ | 91–93 |
| H | $N(CH_3)_2$ | $C_8H_{17}NH_2$ | $C_8H_{17}-$ | $CH_3NCO$ | H | $CH_3-$ | 91–93 |
| $CH_3$ | $N(CH_3)_2$ | $C_8H_{17}NH_2$ | $CH_3$ | $CH_3NCO$ | H | $CH_3-$ | |
| H | $N(CH_3)_2$ | $C_{18}H_{37}NH_2$ | $C_{18}H_{37}$ | $CH_3NCO$ | H | $CH_3-$ | |
| H | $N(CH_3)_2$ | $C_4H_9OCH_2CH_2NH_2$ | $C_4H_9OCH_2CH_2-$ | $CH_3NCO$ | H | $CH_3-$ | |
| H | $N(CH_3)_2$ | $CH_3OCH_2CH_2CH_2NH_2$ | $CH_3OCH_2CH_2CH_2-$ | $CH_3NCO$ | H | $CH_3-$ | Vis. liq IR: 3.0(NH); 5.78 (CO) |
| H | $NHCH_3$ | 2-amino-3-methylthiophene | 3-methylthienyl | $CH_3NCO$ | H | $CH_3-$ | |
| H | $NHC_2H_5$ | 2-aminothiophene | thienyl | $CH_3NCO$ | H | $CH_3-$ | |
| $CH_3$ | $OC_2H_5$ | $CH_3ONH_2-HCl$ | $CH_3O-$ | $CH_3NCO$ | H | $CH_3-$ | 159–164 |

TABLE I.A.

| Compound of Formula III | | | Compound of Formula II | | Compound of Formula I | | | Melting Point |
|---|---|---|---|---|---|---|---|---|
| A | Q | Amine | $R_7$ | Isocyanate | $R_2$ | R | $R_3$ | (° C.) |
| H | $N(CH_3)_2$ | $NH_2OH-HCl$ | $HO-$ | $CH_3NCO$ (2 molar equivalents) | H | $CH_3NH\overset{\overset{O}{\|}}{C}O-$ | $CH_3-$ | 169.5–170.5 |
| H | $OCH_3$ | $NH_2OH-HCl$ | $HO-$ | $CH_3NCO$ (2 molar equivalents) | H | $CH_3NH\overset{\overset{O}{\|}}{C}O-$ | $CH_3-$ | |
| H | $OC_2H_5$ | $NH_2OH-HCl$ | $HO-$ | $CH_3NCO$ (2 molar equivalents) | H | $CH_3NH\overset{\overset{O}{\|}}{C}O-$ | $CH_3-$ | |
| H | $-NHCH_2CH(CH_3)_2$ | $NH_2OH-HCl$ | $HO-$ | $CH_3NCO$ (2 molar equivalents) | H | $CH_3NH\overset{\overset{O}{\|}}{C}O-$ | $CH_3-$ | |

EXAMPLE 2

A mixture of 142 parts of N,N-dimethyl-2-hydroxyiminoacetoacetamide (a compound of Formula III), 1200 parts of toluene, 123 parts of p-anisidine and 1 part of p-toluenesulfonic acid was refluxed overnight in a flask fitted with a Dean-Stark distilling trap and water condenser. Eighteen parts of water were removed in this manner. On cooling, a heavy slurry of solid product precipitated. This was filtered and washed with butyl chloride thereby providing a product which melted at 201.5°–203° C. Recrystallization from acetonitrile gave 151 parts of N,N-dimethyl-2-hydroxyimino-3-(4-methoxyphenylimino)butyramide (a compound of Formula II) as a yellow solid, m.p. 204°–205.5° C.

In a similar manner to Example 2, the following "Compounds of Formula II" in Table II, following, can be made by substituting essentially stoichiometric ratios of the indicated "Compound of Formula III" and "Amine". In some instances, the toluenesulfonic acid catalyst used in the above example is unnecessary. In others, benzene is a satisfactory solvent.

TABLE II

| Compound of Formula III | | | Compound of Formula II | | Compound of Formula I | | Melting Point |
|---|---|---|---|---|---|---|---|
| A | Q | Amine | $R_7$, R of Form. I | Isocyanate | $R_2$ | $R_3$ | (° C.) |
| H | $-N(CH_3)_2$ | phenyl-$NH_2$ | phenyl | $CH_3NCO$ | H | $CH_3$ | 155–157.5 |
| H | $-NHC_2H_5$ | phenyl-$NH_2$ | phenyl | $CH_3NCO$ | H | $CH_3$ | |

TABLE II-continued

| | | | | | | | |
|---|---|---|---|---|---|---|---|
| H | —N(CH₃)₂ | 2-CH₃-C₆H₄-NH₂ (2-methylaniline) | 2-CH₃-C₆H₄— | CH₃NCO | H | CH₃ | 121–124.5 |
| H | —N(CH₃)₂ | 3-CH₃-C₆H₄-NH₂ | 3-CH₃-C₆H₄— | CH₃NCO | H | CH₃ | 125–130 |
| H | —N(CH₃)₂ | 3-CH₃-C₆H₄-NH₂ | 3-CH₃-C₆H₄— | C₂H₅NCO | H | C₂H₅ | |
| CH₃ | —N(CH₃)₂ | 3-CH₃-C₆H₄-NH₂ | 3-CH₃-C₆H₄— | CH₃NCO | H | CH₃ | |
| H | —N(CH₃)₂ | 3-CH₃-C₆H₄-NH₂ (3-methyl, NH₂ para) | 3-CH₃-C₆H₄— | CH₃NCO | H | CH₃ | 160.5–162 |
| H | —N(CH₃)₂ | 2-OCH₃-C₆H₄-NH₂ | 2-OCH₃-C₆H₄— | CH₃NCO | H | CH₃ | 162–164 |
| H | —N(CH₃)₂ | 3-OCH₃-C₆H₄-NH₂ | 3-OCH₃-C₆H₄— | C₂H₅NCO | H | C₂H₅— | |
| H | —N(CH₃)₂ | 3,5-(CH₃O)₂-C₆H₃-NH₂ | 3,5-(CH₃O)₂-C₆H₃— | CH₃NCO | H | CH₃— | 175–177 |
| H | —NHCH₃ | 3,5-(CH₃O)₂-C₆H₃-NH₂ | 3,5-(CH₃O)₂-C₆H₃— | CH₃NCO | H | CH₃— | |
| H | —N(CH₃)₂ | 3-CH₃S-C₆H₄-NH₂ | 3-CH₃S-C₆H₄— | CH₃NCO | H | CH₃ | 169–170 |
| H | —N(CH₃)₂ | 2-F-C₆H₄-NH₂ | 2-F-C₆H₄— | CH₃NCO | H | CH₃ | 176–177.5 |
| H | —N(CH₃)₂ | C₆H₅-NH₂ | 2-F-C₆H₄— | C₂H₅NCO | H | CH₃ | |
| H | —N(CH₃)₂ | 3-F-C₆H₄-NH₂ | 3-F-C₆H₄— | CH₃NCO | H | CH₃ | 170–172 |
| CH₃ | —N(C₂H₅)₂ | 3-F-C₆H₄-NH₂ | 3-F-C₆H₄— | CH₃NCO | H | CH₃ | 170–172 |

TABLE II-continued

| Compound of Formula III | | Amine | Compound of Formula II R₇ | Isocyanate | Compound of Formula I | | Melting Point (° C.) |
|---|---|---|---|---|---|---|---|
| A | Q | | | | R₂ | R₃ | |
| CH₃ | —N(C₂H₅)₂ | F-C₆H₃(NH₂) | F-C₆H₃— | CH₃NCO | H | CH₃ | |
| CH₃ | —N(C₂H₅)₂ | F-C₆H₃(NH₂) | F-C₆H₃— | CH₂=CHCH₂NCO | H | CH₂=CHCH₂— | |
| H | —N(CH₃)₂ | (CH₃)₂N-C₆H₄-NH₂ | (CH₃)₂N-C₆H₄— | CH₃NCO | H | CH₃ | 156–157 |
| CH₃ | —N(C₂H₅)(C₄H₉) | morpholine-N—NH₂ | morpholine-N— | CH₃NCO | H | CH₃ | |
| H | —N(CH₃)(C₄H₉) | (C₂H₅)₂NNH₂ | (C₂H₅)₂N— | CH₃NCO | H | CH₃ | |
| H | —NHCH₂CH=CH₂ | CH₃O-(thiophene-S)-NH₂ | CH₃O-(thiophene-S)— | CH₃NCO | H | CH₃ | |
| H | —N(CH₃)₂ | 2,5-(CH₃)₂-thiophene-NH₂ | 2,5-(CH₃)₂-thiophene— | CH₃NCO | H | CH₃ | |
| H | —N(CH₃)₂ | C₆H₁₁CH₂NH₂ | C₆H₁₁CH₂— | CH₃NCO | H | CH₃ | |
| H | —N(CH₃)₂ | C₆H₁₁CH₂CH₂NH₂ | C₆H₁₁CH₂CH₂— | CH₃NCO | H | CH₃ | |

| Compound of Formula III | | Amine | Compound of Formula II R₇R of Form. I | Isocyanate | Compound of Formula I | | Melting Point (° C.) |
|---|---|---|---|---|---|---|---|
| A | Q | | | | R₂ | R₃ | |
| H | —NHCH₃ | C₄H₉CH(C₂H₅)CH₂NH₂ | C₄H₉CH(C₂H₅)CH₂— | CH₃NCO | H | CH₃ | |
| H | —N(CH₃)₂ | (thiophene-S)-CH₂NH₂ | (thiophene-S)-CH₂— | CH₃NCO | H | CH₃ | |
| H | —N(CH₃)₂ | CH₃-C₆H₄-NH₂ | CH₃-C₆H₄— | C₂H₂NCO | H | CH₃ | |
| H | —OCH₃ | C₆H₅NH₂ | C₆H₅— | CH₃NCO | H | CH₃ | |
| CH₃ | —N(CH₃)₂ | cyclopentyl-CH(CH₃)NH₂ | cyclopentyl-CH(CH₃)— | CH₃NCO | H | CH₃ | |
| H | —N(CH₃)₂ | CH₂=C(CH₃)CH₂NH₂ | CH₂=C(CH₃)CH₂— | CH₃NCO | H | CH₃ | |
| H | —N(morpholino) | CH₃O-C₆H₄-NH₂ | CH₃O-C₆H₄— | CH₃NCO | H | CH₃ | |
| H | —N(CH₂)₂ | (thiophene-S)-NH₂ | (thiophene-S)— | CH₃NCO | H | CH₃ | 161–162 |

TABLE II-continued

| | | | | | | |
|---|---|---|---|---|---|---|
| H | —N(CH$_3$)$_2$ | 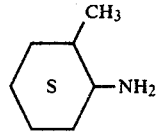 | 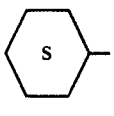 | CH$_3$NCO | H CH$_3$ | 143–145 |

EXAMPLE 3

A mixture of 7.6 parts ethyl 2-hydroxyimino-3-methoxyiminovalerate was mixed with 7 parts 40% aqueous methylamine solution at 25° C. and stirred till homogeneous (5 minutes). The mixture was allowed to stand 18 hours and then evaporated under reduced pressure (15 mm) at 50° C. water-bath temperature to dryness. Recrystallization of the residue from acetonitrile gave 4.3 parts of N-methyl-2-hydroxyimino-3-methoxyiminovaleramide, m.p. 168°–170° C.

The compounds tabulated in Table III can be prepared according to the procedure of Example 3 by substituting comparable stoichiometric amounts of the indicated "Compound of Formula II (Q=OR$_4$)" and "Amine" to produce the "Compound of Formula II (Q=NR$_5$R$_6$)". Some variations in solvent systems, reaction times, and use of catalyst can be made as discussed previously.

TABLE III

| A | Compound of Formula II (Q=OR4) | | | Compound of Formula II (Q=NR5R6) | | | Compound of Formula I | | |
|---|---|---|---|---|---|---|---|---|---|
| | R4 | R7 | Amine | R5 | R6 | Isocyanate | R | R2 | R3 |
| H | CH3 | CH3O— | CH3NH2 | CH3 | H | CH3NCO | CH3O— | H | CH3— |
| H | C2H5 | C3H7O— | CH3NH2 | CH3 | H | C2H5NCO | C3H7O— | H | C2H5— |
| H | C2H5 | (CH3)2N— | CH3NH2 | CH3 | H | CH2=CHCH2NCO | (CH3)2N— | H | CH2=CHCH2— |
| H | CH3 | CH3— | (CH3)2NH | CH3 | CH3 | CH3NCO | CH3— | H | CH3— |
| CH3 | C2H5 | C8H17— | C4H9N(CH3)H | C4H9 | CH3 | CH3NCO | C8H17— | H | |
| CH3 | C2H5 | 4-CH3O-C6H4— | CH2=CHCH2NH2 | CH2=CHCH2— | H | CH3NCO | 4-CH3O-C6H4— | | CH3— |
| H | CH3 | HO— | CH2CH2–NH–CH2CH2 (aziridine) | —CH2CH2CH2CH2— | | CH3NCO (2 molar equivalents) | —OCNHCH3 (C=O) | H | CH3— |

EXAMPLE 4

A mixture of 34 parts of N,N-dimethyl-2-hydroxyimino-3-methoxyiminobutyramide, 350 parts of methylene chloride, 13 parts of methyl isocyanate and one-tenth part triethylenediamine was stirred at 25° C. for 3 hours and then refluxed for 1 hour. The solvent was removed by stripping under reduced pressure (15 mm.) at 50° bath temperature, thereby affording the solid crude product. Recrystallization from a benzene-acetonitrile mixture gave 32 parts of N,N-dimethyl-3-methoxyimino-2-[(methylcarbamoyl)oximino]butyramide, m.p. 172°-173° C.

The procedure of Example 4 can be repeated substituting comparable stoichiometric amounts of the indicated "Compound of Formula II" and "Isocyanate" to produce the "Compound of Formula I". Some variations in solvent systems, reaction times, and catalyst can be made as discussed previously (see Tables I, II, and III).

EXAMPLE 5

To a stirred mixture of 75 parts of N,N-dimethyl-2-hydroxyimino-3-methoxyiminobutyramide and 1500 parts of tetrahydrofuran was added portionwise over a fifteen-minute period 19 parts of 50% sodium hydride, mineral oil dispersion. The temperature was maintained in the range of 20° C. to 30° C. After about one-half hour, evolution of hydrogen gas ceased, and rapid addition of 55 parts diethylcarbamoyl chloride was begun. The temperature spontaneously rose to 33° C., and rapid thinning-out of the oxime salt slurry occurred. The mixture was refluxed and stirred for three hours. The inorganic solids were then removed by filtration and the product recovered by removal of the solvent under reduced pressure. The residue was twice triturated with hexane and the liquid decanted to remove the mineral oil. After drying, there was obtained 90 parts of N,N-dimethyl-2-[(diethylcarbamoyl)oxyimino]-3-methoxyiminobutyramide, m.p. 59°-61°.

The compounds tabulated in Table IV, following, can be prepared according to the procedure of Example 5 using the indicated "Compound of Formula II" and "Carbamoyl Chloride" to produce the corresponding "Compound of Formula I".

TABLE IV

| Compound of Formula II | | | Carbamoyl | Compound of Formula I | | Melting Point |
|---|---|---|---|---|---|---|
| A | Q | $R_7$, R of Form. I | Chloride | $R_2$ | $R_3$ | (° C.) |
| H | $N(CH_3)_2$ | $CH_3O-$ | $(C_2H_5)_2NCCl$, $\|$ O | $C_2H_5-$ | $C_2H_5-$ | 59-61 |
| H | morpholino (N—O ring) | thiopyranyl (S ring) | $(CH_3)_2NCCl$, O | $CH_3-$ | $CH_3-$ | |
| H | N-methylpiperazinyl (N—NCH$_3$ ring) | $CH_3O-$ | $(CH_3)_2NCCl$, O | $CH_3-$ | $CH_3-$ | b.p. 193 at 0.5 mm. |
| H | $N(CH_3)(OCH_3)$ | $CH_3O-$ | $(CH_3)_2NCCl$, O | $CH_3-$ | $CH_3-$ | 87-89 |
| H | $N-(CH_3)_2$ | $CH_3O$-phenyl-O- | $(CH_3)_2NCCl$, O | $CH_3-$ | $CH_3-$ | 108-110 |
| $CH_3$ | $NHCH_3$ | $CH_3$-phenyl-O- | $(CH_3)_2NCCl$, O | $CH_3-$ | $CH_3-$ | |
| H | $N(CH_3)_2$ | $CH_3S$-phenyl-O- | $(CH_3)_2NCCl$, O | $CH_3-$ | $CH_3-$ | 122-124 |
| H | $OC_2H_5$ | $CH_3S$-phenyl-O- | $(CH_3)_2NCCl$, O | $CH_3-$ | $CH_3-$ | |
| H | $N(CH_3)_2$ | $CH_3$-phenyl-O- | $(CH_3)_2NCCl$, O | $CH_3-$ | $CH_3-$ | 107-109 |
| H | $N(CH_3)_2$ | $CH_3$-phenyl- | $(CH_3)_2NCCl$, O | $CH_3-$ | $CH_3-$ | |

TABLE IV-continued

| Compound of Formula II | | | Carbamoyl | Compound of Formula I | | Melting Point |
| --- | --- | --- | --- | --- | --- | --- |
| A | Q | $R_7$, R of Form. I | Chloride | $R_2$ | $R_3$ | (° C.) |
| H | $N(CH_3)_2$ | (CH$_3$)$_2$N—⟨cyclohexanone⟩ | $(CH_3)_2NCCl$ (C=O) | $CH_3$— | $CH_3$— | 138–141.5 |
| H | $N(CH_3)_2$ | $(CH_3)_2N$— | $(CH_3)_2NCCl$ (C=O) | $CH_3$— | $CH_3$— | Liq. IR:3.0(NH); 5.8(CO) |
| H | $N(CH_3)_2$ | morpholine-N— | $(CH_3)_2NCCl$ (C=O) | $CH_3$— | $CH_3$— | 142–144 (dec) |
| H | $OC_2H_5$ | $CH_3O$— | $(CH_3)_2NCCl$ (C=O) | $CH_3$— | $CH_3$— | Liq. IR:3.1(NH); 5.78(CO, carbamate); 5.82(CO,ester) |
| H | $OC_2H_5$ | $CH_3O$— | $(C_2H_5)_2NCCl$ (C=O) | $C_2H_5$ | $C_2H_5$ | |
| $CH_3$ | $OCH_3$ | $(CH_3)_2N$— | $(CH_3)_2NCCl$ (C=O) | $CH_3$— | $CH_3$— | |
| H | $N(CH_3)_2$ | $CH_3$— | $(CH_3)_2NCCl$ (C=O) | $CH_3$— | $CH_3$— | |
| $CH_3$ | $N(CH_3)(C_2H_5)$ | $t\text{-}C_4H_9$ | $(C_2H_5)_2CCl$ (C=O) | $C_2H_5$ | $CH_3$ | |
| H | $N(C_2H_5)(C_4H_9)$ | $CH_3O$— | $(CH_3)_2NCCl$ (C=O) | $CH_3$— | $CH_3$— | |
| H | hexamethyleneimino | $CH_3O$— | $(CH_3)_2NCCl$ (C=O) | $CH_3$— | $CH_3$— | |
| H | thiazolidino | $C_3H_7O$— | $(CH_3)_2NCCl$ (C=O) | $CH_3$— | $CH_3$— | |
| $CH_3$ | thiazolidino | $C_2H_5O$— | $C_2H_5(CH_2=CHCH_2)NCCl$ (C=O) | $C_2H_5$ | $CH_2=CHCH_2$— | |
| H | $NHC_2H_5$ | $(CH_3)_2N$— | $CH_3(CH_2=CHCH_2)NCCl$ (C=O) | $CH_3$— | $CH_2=CHCH_2$— | |
| H | $NHOCH_3$ | C$_6$H$_5$— | $(CH_3)_2NCCl$ (C=O) | $CH_3$— | $CH_3$— | |
| H | $N(CH_3)_2$ | (CH$_3$)$_2$N—C$_6$H$_4$— | $(CH_3)_2NCCl$ (C=O) | $CH_3$— | $CH_3$— | |
| H | $N(CH_3)_2$ | F—C$_6$H$_4$— | $(CH_3)_2NCCl$ (C=O) | $CH_3$— | $CH_3$— | |
| H | $N(CH_3)_2$ | $CH_3CH_2CH_2$— | $(CH_3)_2NCCl$ (C=O) | $CH_3$— | $CH_3$— | $N_D^{25} = 1.4842$ |
| H | $N(CH_3)_2$ | $CH_3(CH_2)_5$— | $(CH_3)_2NCCl$ (C=O) | $CH_3$— | $CH_3$— | $N_D^{25} = 1.4842$ |
| H | $N(CH_3)_2$ | $CH_3CH_2$— | $(CH_3)_2NCCl$ (C=O) | $CH_3$— | $CH_3$— | $N_D^{25} = 1.4842$ |
| H | $N(CH_3)_2$ | $CH_3$— | $(CH_3)_2NCCl$ (C=O) | $CH_3$— | $CH_3$— | 130–132° |
| H | $N(CH_3)_2$ | $CH_3O$— | $(CH_3)_2NCCl$ (C=O) | $CH_3$— | $CH_3$— | 102–103.5° |

TABLE IV.A.

| Compound of Formula II | | | Carbamoyl Chloride | Compound of Formula I | | | Melting Point (° C.) |
|---|---|---|---|---|---|---|---|
| A | Q | $R_7$ | | $R_2$ | R | $R_3$ | |
| H | $N(CH_3)_2$ | HO | $(CH_3)_2NCCl$ (2 molar equivalents) $\parallel$ O | $CH_3-$ | $(CH_3)_2N\overset{\overset{O}{\parallel}}{C}-O-$ | $CH_3-$ | 1  117-120 |
| H | $OCH_3$ | HO | $(CH_3)_2NCCl$ (2 molar equivalents( $\parallel$ O | $CH_3-$ | $(CH_3)_2N\overset{\overset{O}{\parallel}}{C}O-$ | $CH_3-$ | |

Formulation and Use

Useful formulations of the compounds of Formula I for control of aphids can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations can be described broadly as consisting essentially of about 1% to 99% by weight of active ingredient(s) and at least one of (a) about 0.1% to 20% surfactant(s) and (b) about 5% to 99% solid or liquid diluent(s). (The expression "consisting essentially of" is used to indicate that in addition to the essential ingredients, i.e. those specifically recited, the formulations can contain other ingredients provided they do not destroy the aphicidal usefulness of the formulations.) More specifically, the formulations contain these ingredients in the following approximate proportions:

| | Percent by Weight | | |
|---|---|---|---|
| | Active Ingredient | Diluent(s) | Surfactant(s) |
| Wettable Powders | 20-90 | 0-74 | 1-10 |
| Oil Suspensions, tions (including emulsifiable concentrates) | 5-50 | 40-95 | 0-15 |
| Aqueous Suspensions | 10-50 | 40-84 | 1-20 |
| Dusts | 1-25 | 70-99 | 0-5 |
| Granules and Pellets | 1-95 | 5-99 | 0-15 |
| High Strength Compositions | 90-99 | 0-10 | 0-2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Edn., Dorland Books, Caldwell, N.J. The more absorptive diluents are preferred for wettable powders and the denser ones for dusts. Typical liquid diluents and solvents are described in Marsden, "Solvents Guide", 2nd Edn., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, New Jersey, as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 4th Edn., McGraw-Hill, N.Y., 1963, pp. 8-59ff.

For further information regarding the art of formulation, see for example:

J. B. Buchanan, U.S. Pat. No. 3,576,834, Apr. 27, 1971, Col. 5, Line 36 through Col. 7, Line 70 and Ex. 1-4, 17, 106, 123-140.

R. R. Schaffer, U.S. Pat. No. 3,560,616, Feb. 2, 1971, Col. 3, Line 48 through Col. 7, Line 26 and Ex. 3-9, 11-18.

E. Somers, "Formulation", Chapter 6 in Torgeson, "Funcigides", Vol. I, Academic Press, New York, 1967.

EXAMPLE 6

| Wettable Powder | Percent |
|---|---|
| Compound of Formula I where A = H, Q = $N(CH_3)_2$, R = $OCH_3$, $R_2$ = H, and $R_3$ = $CH_3$ | 40 |
| Dioctyl sodium sulfosuccinate | 1.5 |
| Sodium ligninsulfonate | 3 |
| Low-viscosity methyl celloluse | 1.5 |
| Attapulgite | 54 |

The ingredients are thoroughly blended, passed through an air mill to produce an average particle size under 15 microns, reblended, and sifted through a U.S.S. No. 50 sieve (0.3 mm. opening) before packaging.

All compounds of Formula I may be formulated in the same manner.

EXAMPLE 7

| Water-soluble Powder | Percent |
|---|---|
| Compound of Formula I where A = H, Q = $N(CH_3)_2$, R = $OCH_3$, $R_2$ and $R_3$ = $CH_3$ | 95 |

-continued

| Water-soluble Powder | Percent |
|---|---|
| Dioctyl sodium sulfosuccinate | 0.5 |
| Sodium ligninsulfonate | 1.0 |
| Synthetic fine silica | 3.5 |

The ingredients are blended and coarsely ground in a hammer mill so that only a few percent of the active exceeds 250 microns (U.S.S. No. 60 sieve) in size. When added to water with stirring, the coarse powder initially disperses and then the active ingredient dissolves so that no further stirring is needed during application.

EXAMPLE 8

| Liquid Concentrate | Percent |
|---|---|
| Compound of Formula I where $A = H$, $Q = N(CH_3)_2$, $R = OCH_3$, $R_2 = CH_3$, and $R_3 = CH_3$ | 31 |
| 24/76 Wt. ratio methanol/water solvent | 68.5 |
| 85% $H_3PO_4$ | 0.5 |

The compound of Formula I and the $H_3PO_4$ are added to the solvent system. The mixture is agitated until a solution is obtained. The solution is clarified by filtration, if necessary.

EXAMPLE 9

| Granules | Percent |
|---|---|
| Compound of Formula I where $A = H$, $Q = N(CH_3)_2$, $R = N(CH_3)_2$, $R_2 = H$, and $R_3 = CH_3$ | 5 |
| Celatom MP78 (diatomaceous earth) granules | 95 |

The compound of Formula I is dissolved in enough methanol to thoroughly wet the granules when blended with them. Enough compound of Formula I is dissolved in the methanol. This solution is added to the granules, and the mixture is agitated to uniformly wet the granules. The methanol solvent is removed by evaporation.

EXAMPLE 10

| Dust | Percent |
|---|---|
| Compound of Formula I where $A = H$, $Q = N(CH_3)_2$, $R = N(CH_3)_2$, $R_2 = CH_3$, and $R_3 = CH_3$ | 10 |
| Attapulgite | 10 |
| Talc | 80 |

The active ingredient is blended with attapulgite and then passed through a hammer mill to produce particles substantially all below 200 microns. The ground concentrate is then blended with powdered talc until homogeneous.

The compounds of this invention are useful for control of aphids which attack plants. When applied to aphids or to the locus of aphid infestation, these pests are killed or driven from the plants. The preferred compounds of this invention are particularly useful in protecting plants from aphids. The compounds are highly systemic and are translocated upwards from both soil and foliar applications. They have a very low order of phytotoxicity and exhibit good safety margins whether applied to foilage or to soil. While they degrade in the biosphere in a reasonable period of time, they are not so short lived as to lose effectiveness immediately upon application. Consequently, cost for control of aphids is not excessive. The preferred compounds are water soluble and can be inexpensively formulated in aqueous systems. Once a spray solution is prepared, no agitation is required to maintain a uniform concentration. After treatment the aphids drop from the plant leaving clean leaf tissue. This is important on green leafy vegetables where the leaves are consumed as food for humans. Some insecticides kill so rapidly that the aphids do not have time to withdraw their beak and, therefore, remain attached to the leaf. These dead aphids are not easily washed or removed from the leaves and lower the quality and desirability of the produce as food.

When applied as a foliar spray the compounds readily penetrate the leaves of plants and move freely within the tissue. Once within the plant they cannot be washed off by rain. The spray does not need to be uniformly distributed over the surface to be effective, nor does it need to contact the aphids per se. When applied to soil, the compounds are absorbed through the roots of the plants and are translocated upward to the leaf tissue on which the aphids are feeding. The soil acts as a reservoir making the compounds available to the plants over a prolonged period of time. The quantity applied to the soil can be calculated to supply the plants with sufficient material to last through the cool part of the season during which aphids are most destructive. Greater quantities will need to be applied where the aphid season is longer or where overlapping species prolong the season. Soil applications minimize harm to naturally occurring parasites and predators and fit well into an integrated pest control program. The term "applying to the plant" includes application to the plant foliage or through the soil.

The quantities of the compounds needed to control aphids depend on many factors such as intensity of the infestation, time of year, species of aphid, species of plant, type of application, frequency and amount of rainfall, temperature and others. As low as 1 ppm in a foliar spray applied to run-off or 200 grams per hectare applied in the row can give control of mild infestations under conditions favorable to the compound. Larger amounts, up to about 10,000 ppm in a foliar spray or 25 kilograms per hectare, are required as the conditions conducive to the compound become adverse. Preferred under practical conditions are concentrations of from 20–1000 ppm and soil rates of 0.5–12.5 kg/ha. Most preferred are concentrations of 40–250 ppm and soil rates of 1.2–2.5 kg/ha.

Aphids controlled by the compounds of this invention include but are not limited to the black bean aphid, *Aphis fabae;* the green peach aphid, *Myzus persicae;* the apple aphid, *Aphis pomi;* the potato aphid, *Macrosiphum euphorbiae;* the green bug, *Toxoptera graminum;* the corn root aphid, *Anuraphis maidiradicis,* cabbage aphid, *Brevicoryne brassicae;* and green citrus aphid, *Aphis spiraecola.*

The compounds of this invention can be mixed with other agricultural chemicals for application to either foliage or soil. Such mixtures broaden the scope of the pests controlled, save costs of multiple applications, and can result in unusual beneficial effects. Soil applications with low rates of oxamyl provide for improved aphid control along with control of nematodes, thrips and other early season insects. Foliar applications in combination with benomyl provide good control of such fungi as apple scab and powdery mildew along with good aphid control on apples. Many other mixtures provide useful results.

Aphicidal activity of compounds of formula I is shown by the results of the following tests:

Test 1-Control of Black Bean Aphids via Foliar Spray

The test units used to demonstrate aphicidal effectiveness through foliar application consisted of two excised nasturtium leaves contained in a 2-ounce narrow mouthed bottle. The bottle contained water for the plant tissue, and cotton was packed around the stems in the neck of the bottle to prevent the spray solution from contacting the water. The two leaves supported approximately 80 aphids in various stages of growth. The test units were sprayed to run off with various concentrations of the compounds made up in aqueous solution containing 1:3000 parts of sodium lauryl sulfate surfactant. Results were observed 1 day after application and are set forth below.

| Compound | Spray Concentrations (%) | % Control |
|---|---|---|
| N,N-dimethyl-3-methoxy-imino-2-[(dimethylcarbamoyl)oxyimino]butyramide | .002 | 100 |
| | .001 | 98 |
| | .0005 | 100 |
| | .00025 | 100 |
| | .0001 | 96 |
| N,N-dimethyl-3-methoxy-imino-2-[(methylcarbamoyl)oxyimino]butyramide | .001 | 100 |
| | .0005 | 100 |
| | .00025 | 97 |
| | .0001 | 76 |
| N,N-dimethyl-2-[(ethylcarbamoyl)oxyimino]-3-methoxyiminobutyramide | .005 | 100 |
| | .002 | 98 |
| | .001 | 95 |
| | .0005 | 88 |
| N,N-dimethyl-2-[(methylcarbamoyl)oxyimino]-3-dimethylhydrazonobutyramide | .001 | 100 |
| | .0005 | 99 |
| | .00025 | 96 |
| | .0001 | 54 |
| N,N-dimethyl-3-(4-methoxyphenylimino)-2-[(methylcarbamoyl)oxyimino]butyramide | .01 | 100 |
| | .005 | 96 |
| | .002 | 64 |
| N,N-dimethyl-3-dimethylhydrazono-2-[(dimethylcarbamoyl)oxyimino]butyramide | .005 | 100 |
| | .001 | 100 |
| | .0005 | 100 |
| | .00025 | 99 |
| | .0001 | 92 |
| None | — | 0 |

Test 2-Systemic Control of Black Bean Aphids

The systemic nature of the compounds was demonstrated by preparing test units as described in Test 1, but substituting solutions of the compounds at the indicated concentrations for the water in which the excised nasturtium leaves were placed. Results were observed one day later and are recorded below.

| Compound | Solution Concentrations (%) | % Control |
|---|---|---|
| N,N-dimethyl-3-methoxy-imino-2-[(dimethylcarbamoyl)oxyimino]butyramide | .01 | 99 |
| | .005 | 98 |
| | .002 | 0 |
| N,N-dimethyl-3-methoxy-imino-2-[(methylcarbamoyl)oxyimino]butyramide | .005 | 100 |
| | .002 | 99 |
| | .0005 | 99 |
| | .00025 | 99 |
| | .0001 | 79 |
| N,N-dimethyl-2-[(ethylcarbamoyl)oxyimino]-3-methoxyiminobutyramide | .01 | 99 |
| | .005 | 99 |
| | .001 | 94 |
| | .0005 | 80 |
| N,N-dimethyl-2-[(methylcarbamoyl)oxyimino]-3-dimethylhydrazonobutyramide | .001 | 100 |
| | .0005 | 99 |
| | .00025 | 96 |
| | .0001 | 54 |
| N,N-dimethyl-3-(4-methoxyphenylimino)-2-[(methylcarbamoyl)oxyimino]butyramide | .01 | 100 |
| | .005 | 96 |
| | .002 | 64 |
| N,N-dimethyl-3-dimethylhydrazono-2-[(dimethylcarbamoyl)oxyimino]butyramide | .005 | 100 |
| | .001 | 100 |
| | .0005 | 97 |
| | .00025 | 99 |
| | .0001 | 95 |
| None | — | 0 |

Test 3-Leaf Penetration by N,N-dimethyl-3-methoxyimino-2-[(dimethylcarbamoyl)oxyimino]butyramide A stock solution of N,N-dimethyl-3-methoxyimino-2-[(dimethylcarbamoyl)oxyimino]butyramide was prepared by dissolving 20 mg. of the compound in 10 ml. of acetone, adding 1 ml. of a 1% methocel suspension and diluting to 50 ml. with water containing 6 drops of sodium lauryl sulfate surfactant per 500 ml. Subsequent dilutions were made with the water-surfactant mixture. Three drops of each of the test dispersions indicated below were spread over the top side of each nasturtium leaf. Aphids were left undisturbed on the lower surface. Data set forth below indicates control of black bean aphids one day after treatment.

| Compound | Concentrations(%) | % Control |
|---|---|---|
| N,N-dimethyl-3-methoxy-imino-2-[(dimethylcarbamoyl)oxyimino]butyramide | .04 | 100 |
| | .02 | 98 |
| | .01 | 98 |
| None | — | 0 |

These results indicate effective penetration of the leaf surface by the compound and translocation within the leaf sufficient to control aphids feeding on the lower surface.

Test 4-Control of Apple Aphids with Foliar Sprays of N,N-dimethyl-3-methoxyimino-2-[(dimethylcarbamoyl)oxyimino]butyramide Small branches of apple trees each infested with approximately 300 apple aphids were placed in small vases of water and the foliage sprayed to run-off with aqueous solutions of N,N-dimethyl-3-methoxyimino-2-[(dimethylcarbamoyl)oxyimino]butyramide at various concentrations. The control branch was sprayed with water alone. Results were observed 1 day later and are recorded below.

| Compound | Spray Concentrations (%) | % Control |
|---|---|---|
| N,N-dimethyl-3-methoxy-imino-2-[(dimethylcarbamoyl)oxyimino]butyramide | .001 | 100 |
| | .0005 | 79 |
| | .0001 | 42 |
| None | — | 8 |

Test 5-Control of Black Bean Aphids via Soil Applications of N,N-dimethyl-3-methoxyimino-2-[(dimethylcarbamoyl)oxyimino]butyramide Nasturtium seeds were planted in pots 7.5 cm in diameter containing soil which had been treated at rates of 1 and 5 kg/ha in the row. Ten days later the young plants were artificially infested with black bean aphids. The percent control of aphids on the test plants were observed and recorded one week later. The same soil was again planted to nasturtiums one month after the initial treatment. Ten days later these plants were infested with aphids as before and results read 1 week later. Observations are recorded below.

| Compound | Amount Applied to Soil (Kg/ha)in the row | % Kill of Aphids Time After Treatment | |
|---|---|---|---|
| | | 17 Days | 48 Days |
| N,N-dimethyl-3-methoxy-imino-2-[(dimethyl-carbamoyl)oxyimino]-butyramide | 1 | 100 | 100 |
| | 5 | 100 | 100 |
| None | — | 0 | 0 |

The results of this experiment demonstrate both the excellent upward translocation and good residual properties possessed by the compound.

Test 6-Control of Three Species of Aphid with Soil Applications of N,N-Dimethyl-3-methoxyimino-2-[(dimethylcarbamoyl)oxyimino]butyramide Nasturtium, cabbage and Chinese cabbage plants approximately 8–10 cm in height were infested with black bean aphids, cabbage aphids and green peach aphids, respectively. One week after infestation the soil was treated with a solution of N,N-dimethyl-3-methoxyimino-2-[(dimethylcarbamoyl)oxyimino]butyramide at 1 and 5 kg/ha rates. Seven days later all treated plants were completely free of aphids while all of the control plants were badly damaged by continuously increased aphid feeding.

Test 7-Control of Black Bean Aphid with Seed Treatments of N,N-Dimethyl-3-methoxyimino-2-[(dimethylcarbamoyl)oxyimino]butyramide Ten grams of nasturtium seed were treated with 0.05 g of N,N-dimethyl-3-methoxyimino-2-[(dimethylcarbamoyl)oxyimino]butyramide dissolved in 5 ml of water. An additional ten grams of seed were treated with the same compound at one-fifth that rate. The treated seed was allowed to dry and then planted. Two weeks after sowing the growing plants were infested with black bean aphids. Results were read two weeks later at which time the plants were again infested. Results were read again two weeks later and are recorded below.

| Treatment | Amount Applied Based on Weight of Seed | Chronology of Test Days | % Control of Aphids |
|---|---|---|---|
| N,N-Dimethyl-3-methoxyimino-2-[(dimethylcarbamoyl)oxyimino]-butyramide | .5% | 0 Planted | |
| | | 13 Infested | |
| | | 28 Rated | 100% |
| | | 28 Infested | |
| | | 41 Rated | 100% |
| | .1% | 0 Planted | |
| | | 13 Infested | |
| | | 28 Rated | 100% |
| | | 28 Infested | |
| | | 41 Rated | 30% |

Test 8-Effects of N,N-Dimethyl-3-methoxyimino-2-[(dimethylcarbamoyl)oxyimino]butyramide on Convergent Lady Beetles Lady beetles were sampled in groups of 25 beetles per cage and then sprayed with a 0.1% aqueous solution of N,N-dimethyl-3-methoxyimino-2-[(dimethylcarbamoyl)oxyimino]butyramide. Observations made 48 hours after spraying indicated that no beetles were killed by this treatment.

In an ancillary experiment nasturtium plants growing in soil treated with 10 kg/ha of N,N-dimethyl-3-methoxyimino-2-[(dimethylcarbamoyl)oxyimino]-butyramide were caged with 50 convergent lady beetles. No beetle mortality resulted from their contact with treated plants.

Test 9-Control of Green Apple Aphid with N,N-Dimethyl-3-methoxyimino-2-[(dimethylcarbamoyl)oxyimino]butyramide in a Delaware Orchard Semi-dwarf Red Delicious apple trees in an orchard located at Newark, Delaware, infested with green apple aphids to the extent of approximately 500 aphids/terminal were sprayed with solutions of N,N-dimethyl-3-methoxyimino-2-[(dimethylcarbamoyl)oxyimino]-butyramide at concentrations of 40, 160 and 320 ppm. Each treatment was run in triplicate and results evaluated four days after spraying. Data for two similar tests carried out about six weeks apart are set forth below.

| Treatment | Spray Concentration (ppm) | % Control | |
|---|---|---|---|
| | | Early Test | Late Test |
| N,N-Dimethyl-3-methoxy-imino-2-[(dimethylcarbamoyl)oxyimino]butyramide | 40 | 70 | 80 |
| | 160 | 87 | 89 |
| | 320 | 97 | 98 |
| Untreated Check | 0 | 0 | 0 |

Test 10-Control of Green Citrus Aphid with N,N-Dimethyl-3-methoxyimino-2-[(dimethylcarbamoyl)oxyimino]butyramide in a Florida Citrus Grove Valencia orange trees located in a grove in Bradenton, Florida, were selected for this test. The trees were in a stage of rapid growth and were heavily infested with green citrus aphids. Solutions of N,N-dimethyl-3-methoxyimino-2-[(dimethylcarbamoyl)oxyimino]-butyramide at concentrations of 40, 160 and 320 ppm were applied with a single-nozzle orchard gun. Each treatment was applied in four replicates and results were recorded three days later. Data are expressed for each replicate in terms of the number of 25 leaves selected at random that were found to be infested. The totals for all four replicates of each treatment consequently represent % infestation.

| Treatment | Spray Concentration (ppm) | % Infested Leaves |
|---|---|---|
| N,N-Dimethyl-3-methoxy-imino-2-[(dimethylcarbamoyl)oxyimino]butyramide | 40 | 42 |
| | 160 | 10 |
| | 320 | 7 |
| Untreated Check | 0 | 97 |

Test 11-Effectiveness of Compounds for Aphid Control at the 1% Spray Level

Nasturtium leaflets containing black bean aphids in all stages of growth were selected for testing. These were impaled singly in an upside-down position on a turntable which was rotated beneath a nozzle. Solutions containing 1% of the test compounds in acetone were applied to the leaflets as a spray. After treatment, leaflets were stored for approximately 20 hrs with their stems in water. Aphicidal results, expressed as % control, were then made and are recorded for the compounds tested.

| A | R | $R_2$ | $R_3$ | Q | % Control |
|---|---|---|---|---|---|
| H | —OCH$_3$ | H | CH$_3$ | —N(H)(CH$_3$) | 100 |
| H | —OCH$_3$ | H | CH$_3$ | —N—(C$_2$H$_5$)$_2$ | 100 |
| H | —OCH$_3$ | H | CH$_3$ | —N(morpholino with O) | 100 |
| H | 4-OCH$_3$-phenyl | H | CH$_3$ | —N(CH$_3$)$_2$ | 100 |
| H | 4-OCH$_3$-phenyl | CH$_3$ | CH$_3$ | —N(CH$_3$)$_2$ | 100 |
| H | 3-OCH$_3$-phenyl | H | CH$_3$ | —N(CH$_3$)$_2$ | 100 |
| H | 2-OCH$_3$-phenyl | H | CH$_3$ | —N(CH$_3$)$_2$ | 100 |
| H | phenyl | H | CH$_3$ | —N(CH$_3$)$_2$ | 95 |
| H | —OCH$_3$ | H | CH$_3$ | —O—C$_2$H$_5$ | 100 |
| CH$_3$ | —OCH$_3$ | H | CH$_3$ | —O—C$_2$H$_5$ | 95 |
| H | 4-SCH$_3$-phenyl | CH$_3$ | CH$_3$ | —N(CH$_3$)$_2$ | 100 |
| H | 4-CH$_3$-phenyl | CH$_3$ | CH$_3$ | —N(CH$_3$)$_2$ | 100 |
| H | 3-CH$_3$-thianyl | H | CH$_3$ | —N(CH$_3$)$_2$ | 100 |
| H | —(CH$_2$)$_3$—OCH$_3$ | H | CH$_3$ | —N(CH$_3$)$_2$ | 95 |
| CH$_3$ | —OCH$_3$ | H | CH$_3$ | —N(CH$_3$)$_2$ | 100 |
| H | —OCH$_3$ | CH$_3$ | CH$_3$ | —N(piperazinyl-NCH$_3$) | 100 |
| H | —OCH$_3$ | H | CH$_3$ | —N(OCH$_3$)(CH$_3$) | 100 |
| H | —OCH$_3$ | H | C$_2$H$_5$ | —N(OCH$_3$)(CH$_3$) | 100 |
| H | —OCH$_3$ | H | CH$_3$ | —N(CH$_3$)$_2$ | 100 |
| H | —OCH$_3$ | H | C$_2$H$_5$ | —N(CH$_3$)$_2$ | 100 |
| H | —OCH$_3$ | C$_2$H$_5$ | C$_2$H$_5$ | —N(CH$_3$)$_2$ | 100 |
| H | —OCH$_3$ | H | CH$_2$CH=CH$_2$ | —N(CH$_3$)$_2$ | 100 |
| H | —N(CH$_3$)$_2$ | H | CH$_3$ | —N(CH$_3$)$_2$ | 100 |
| H | —N(CH$_3$)$_2$ | CH$_3$ | CH$_3$ | —N(CH$_3$)$_2$ | 100 |

-continued

| A | R | R2 | R3 | Q | % Control |
|---|---|----|----|---|-----------|
| H | morpholino (−N⌒O) | H | CH$_3$ | −N(CH$_3$)$_2$ | 100 |
| H | piperidino (−N⌒) | H | CH$_3$ | −N(CH$_3$)$_2$ | 95 |
| H | 2-fluorophenyl | H | CH$_3$ | −N(CH$_3$)$_2$ | 100 |
| H | 4-fluorophenyl | H | CH$_3$ | −N(CH$_3$)$_2$ | 100 |
| H | 3-fluorophenyl | H | CH$_3$ | −N(CH$_3$)$_2$ | 100 |
| H | morpholino (−N⌒O) | H | CH$_3$ | −N(CH$_3$)$_2$ | 100 |
| H | 4-methylphenyl | H | CH$_3$ | −N(CH$_3$)$_2$ | 100 |
| H | 2-methylphenyl | H | CH$_3$ | −N(CH$_3$)$_2$ | 95 |
| H | 3-methylphenyl | H | CH$_3$ | −N(CH$_3$)$_2$ | 100 |
| H | 4-(N,N-dimethylamino)phenyl | H | CH$_3$ | −N(CH$_3$)$_2$ | 100 |
| H | thianyl (S-ring) | H | CH$_3$ | −N(CH$_3$)$_2$ | 95 |
| H | morpholino (−N⌒O) | H | CH$_3$ | −OC$_2$H$_5$ | 100 |
| C$_2$H$_5$ | −OCH$_3$ | H | CH$_3$ | −OC$_2$H$_5$ | 100 |
| H | −CH$_3$ | H | CH$_3$ | −N(CH$_3$)$_2$ | 100 |
| H | −CH$_2$CH$_2$CH$_3$ | H | CH$_3$ | −N(CH$_3$)$_2$ | 100 |
| H | −CH$_2$CH$_3$ | H | CH$_3$ | −N(CH$_3$)$_2$ | 100 |
| H | −CH(CH$_3$)$_2$ | H | CH$_3$ | −N(CH$_3$)$_2$ | 100 |
| H | −CH(C$_2$H$_5$)(CH$_3$) | H | CH$_3$ | −N(CH$_3$)$_2$ | 100 |
| H | −n-C$_8$H$_{17}$− | H | CH$_3$ | −N(CH$_3$)$_2$ | 100 |
| H | −n-C$_6$H$_{13}$− | H | CH$_3$ | −N(CH$_3$)$_2$ | 100 |

-continued

| A | R | $R_2$ | $R_3$ | Q | % Control |
|---|---|---|---|---|---|
| H | −N⟨(CH₂)₂O(CH₂)₂⟩ (morpholino) | $CH_3$ | $CH_3$ | $-N(CH_3)_2$ | 100 |
| H | $-CH_3$ | $CH_3$ | $CH_3$ | $-N(CH_3)_2$ | |
| H | $-CH_2-C_6H_5$ | H | $CH_3$ | $-N(CH_3)_2$ | 100 |
| H | $-CH_2CH_2-C_6H_5$ | H | $CH_3$ | $-N(CH_3)_2$ | 100 |
| H | $-(CH_2)_9CH_3$ | H | $CH_3$ | $-N(CH_3)_2$ | 100 |
| H | $-(CH_2)_{17}CH_3$ | H | $CH_3$ | $-N(CH_3)_2$ | 100 |
| H | $-(CH_2)_{17}CH_3$ | $CH_3$ | $CH_3$ | $-N(CH_3)_2$ | 100 |

I claim:

1. An aphicidal composition consisting essentially of (1) at least one of (a) an inert diluent and (b) a surfactant and (2) an aphicidally effective amount of a compound of the formula $$\begin{array}{c} \phantom{ACH_2-C-} \quad\; R-N \;\; N-O-\overset{O}{\overset{\|}{C}}-\overset{R_2}{\underset{|}{N}}-R_3 \\ ACH_2-\overset{\|}{C}-\overset{\|}{C}-\overset{\|}{\underset{O}{C}}-Q \end{array}$$

wherein:
A is hydrogen or methyl;
R is $C_1$–$C_{18}$ alkyl; $C_3$–$C_4$ alkenyl; $C_5$–$C_7$ cycloalkyl optionally substituted with methoxy or with 1 or 2 methyl groups; $C_6$–$C_8$ cycloalkylalkyl; $C_1$–$C_3$ alkoxy; alkoxyalkyl with a total of 3–6 carbon atoms;
$R_2$ is hydrogen, methyl, or ethyl;
$R_3$ is methyl, ethyl, or allyl;
Q is $-NR_5R_6$;
$R_5$ is methoxy, $C_1$–$C_4$ alkyl or allyl;
$R_6$ is hydrogen, methyl, or ethyl;
$R_5$ and $R_6$ can be taken together to form a ring and are
$-(CH_2)_2O(CH_2)_2-$;

$$-(CH_2)_2\overset{CH_3}{\underset{|}{N}}(CH_2)_2-;$$

or $-(CH_2)_n-$; and n is 4–6;
provided that the total carbon content of Q, $R_2$, and $R_3$ is not greater than 8C.

2. The composition of claim 1 wherein
A is hydrogen;
R is $C_5$–$C_7$ cycloalkyl, methylcyclohexyl, allyl, methoxy;
$R_3$ is methyl;
$R_5$ is methyl or ethyl; and
$R_6$ is hydrogen, methyl, or ethyl.

3. The composition of claim 1 wherein R is methoxy.

4. The composition of claim 1 wherein R is $C_1$–$C_{18}$ alkyl; $C_3$–$C_4$ alkenyl; $C_5$–$C_7$ cycloalkyl optionally substituted with methoxy or with one or two methyl groups; $C_6$–$C_8$ cycloalkylalkyl; $C_1$–$C_3$ alkoxy; or alkoxyalkyl with a total of 3–6 carbon atoms.

5. The composition of claim 4 wherein said compound is N,N-dimethyl-2-[(methylcarbamyl)oxyimino]-3-(2-mthylcyclohexylimino)butyramide.

6. The composition of claim 4 wherein said compound is N,N-dimethyl-3-methoxyimino-2-[(methylcarbamyl)oxyimino]-butyramide.

7. The composition of claim 4 wherein said compound is N,N-dimethyl-2-[(dimethylcarbamyl)oxyimino]-3-methoxyiminobutyramide.

8. Method of protecting plants from aphids which comprises applying to the plant an aphicidally effective amount of a compound of the formula $$\begin{array}{c} \phantom{ARC_2-C-} \quad\; R-N \;\; N-O-\overset{O}{\overset{\|}{C}}-\overset{R_2}{\underset{|}{N}}-R_3 \\ ARC_2-\overset{\|}{C}-\overset{\|}{C}-\overset{\|}{\underset{O}{C}}-Q \end{array}$$

wherein:
A is hydrogen or methyl;
R is $C_1$–$C_{18}$ alkyl; $C_3$–$C_4$ alkenyl; $C_5$–$C_7$ cycloalkyl optionally substituted with methoxy or with 1 or 2 methyl groups; $C_6$–$C_8$ cycloalkylalkyl; $C_1$–$C_3$ alkoxy; alkoxyalkyl with a total of 3–6 carbon atoms;
$R_2$ is hydrogen, methyl, or ethyl;
$R_3$ is methyl, ethyl, or allyl;
Q is $-NR_5R_6$;
$R_5$ is methoxy, $C_1$–$C_4$ alkyl or allyl;
$R_6$ is hydrogen, methyl, or ethyl;
$R_5$ and $R_6$ can be taken together to form a ring and are
$-(CH_2)_2O(CH_2)_2-$;

$$-(CH_2)_2\overset{CH_3}{\underset{|}{N}}(CH_2)_2-;$$

or $-(CH_2)_n-$; and n is 4–6;
provided that the total carbon content of Q, $R_2$, and $R_3$ is not greater than 8C.

9. The method of claim 8 wherein
A is hydrogen;
R is $C_5$–$C_7$ cycloalkyl, methylcyclohexyl, allyl, methoxy,
$R_3$ is methyl;
$R_5$ is methyl or ethyl; and
$R_6$ is hydrogen, methyl, or ethyl.

10. The method of claim 9 wherein R is methoxy.

11. The method of claim 8 wherein R is $C_1$–$C_{18}$ alkyl; $C_3$–$C_4$ alkenyl; $C_5$–$C_7$ cycloalkyl optionally substituted with methoxy or with one or two methyl groups;

$C_6$–$C_8$ cycloalkylalkyl; $C_1$–$C_3$ alkoxy; or alkoxyalkyl with a total of 3–6 carbon atoms.

12. The method of claim 11 wherein said compound is N,N-dimethyl-2-[(methylcarbamyl)oxyimino]-3-(2-methycyclohexylimino)butyramide.

13. The method of claim 11 wherein said compound is N,N-dimethyl-3-methoxyimino-2-[(methylcarbamyl)oxyimino]butyramide.

14. The method of claim 11 wherein said compound is N,N-dimethyl-2-[(dimethylcarbamoyl)oxyimino]-3-methoxyiminobutyramide.

* * * * *